United States Patent
Rizk et al.

(10) Patent No.: US 9,066,859 B1
(45) Date of Patent: *Jun. 30, 2015

(54) VISCOELASTIC CLEANSING GEL

(71) Applicant: L'OREAL, Paris (FR)

(72) Inventors: Kirolos Rizk, Helmetta, NJ (US); Miao Wang, Westfield, NJ (US)

(73) Assignee: L'OREAL, Paris (FR)

( * ) Notice: Subject to any disclaimer, the term of this patent is extended or adjusted under 35 U.S.C. 154(b) by 0 days.

This patent is subject to a terminal disclaimer.

(21) Appl. No.: 14/100,156

(22) Filed: Dec. 9, 2013

(51) Int. Cl.
| | | |
|---|---|---|
| *C11D 1/02* | (2006.01) | |
| *C11D 1/38* | (2006.01) | |
| *C11D 1/75* | (2006.01) | |
| *C11D 1/90* | (2006.01) | |
| *C11D 1/94* | (2006.01) | |
| *C11D 3/22* | (2006.01) | |
| *A61Q 5/02* | (2006.01) | |
| *A61K 8/04* | (2006.01) | |
| *A61Q 5/12* | (2006.01) | |

(52) U.S. Cl.
CPC . *A61K 8/042* (2013.01); *A61Q 5/02* (2013.01); *A61Q 5/12* (2013.01)

(58) Field of Classification Search
CPC ............ C11D 1/02; C11D 1/38; C11D 1/662; C11D 1/75; C11D 1/90; C11D 1/94; C11D 3/22; C11D 3/3796; A61Q 5/02
USPC ......... 510/119, 121, 123, 125, 127, 155, 426, 510/433, 474, 475, 490, 504; 424/70.11, 424/70.19, 70.21, 70.24, 70.31
See application file for complete search history.

(56) References Cited

U.S. PATENT DOCUMENTS

| | | | |
|---|---|---|---|
| 5,965,502 A | 10/1999 | Balzer | |
| 6,110,451 A | 8/2000 | Matz et al. | |
| 6,489,286 B1 * | 12/2002 | Lukenbach et al. | 510/475 |
| 6,770,607 B2 | 8/2004 | Chen et al. | |
| 2003/0078172 A1 | 4/2003 | Guiramand et al. | |
| 2004/0097385 A1 | 5/2004 | Chen et al. | |
| 2005/0071933 A1 | 4/2005 | Rondeau | |
| 2006/0135382 A1 * | 6/2006 | Molenda | 510/119 |
| 2006/0217283 A1 | 9/2006 | De Salvert et al. | |
| 2008/0233061 A1 | 9/2008 | Gates et al. | |
| 2008/0242573 A1 | 10/2008 | Wei | |
| 2009/0178210 A1 * | 7/2009 | Bistram | 8/431 |
| 2011/0139170 A1 | 6/2011 | Hippe et al. | |
| 2011/0155163 A1 | 6/2011 | Viravau et al. | |
| 2011/0155164 A1 | 6/2011 | Viravau et al. | |
| 2012/0196783 A1 | 8/2012 | D'Aversa et al. | |
| 2012/0308492 A1 | 12/2012 | Allef et al. | |
| 2013/0112217 A1 * | 5/2013 | Molenda et al. | 132/202 |
| 2013/0143784 A1 | 6/2013 | Rizk | |
| 2013/0164244 A1 | 6/2013 | Molenda et al. | |

FOREIGN PATENT DOCUMENTS

| | | |
|---|---|---|
| EP | 0095238 A2 | 11/1983 |
| EP | 0530974 A1 | 3/1993 |
| EP | 2789896 A1 | 8/2000 |
| EP | 1504749 B1 | 12/2008 |
| WO | 00/48557 A2 | 8/2000 |
| WO | WO-02092050 A2 | 11/2002 |
| WO | 2007/001341 A2 | 1/2007 |
| WO | 2010/069500 A1 | 6/2010 |

OTHER PUBLICATIONS

U.S. Appl. No. 14/100,117, filed Dec. 9, 2013, Kirolos Rizk.
U.S. Appl. No. 14/100,126, filed Dec. 9, 2013, Kirolos Rizk.
U.S. Appl. No. 14/100,144, filed Dec. 9, 2013, Kirolos Rizk.
U.S. Appl. No. 14/100,156, filed Dec. 9, 2013, Kirolos Rizk.
Jorg Kahre, Catherine Le Hen Ferrenbach, Laurence Robbe Tomine, Holger Tesmann, Tensio-Actifs Les alkylpolyglucosides une nouveaute en matiere de soin et de tolerance, Parfums Cosmetiques Actualites No. 131, Nov. 1996, pp. 49-61.
Notification of Transmittal of the International Search Report and the Written Opinion of the International Searching Authority, or the Declaration, as well as the Search Report and Written Opinion, International Application No. PCT/EP2014/077068, dated Mar. 10, 2015.

* cited by examiner

*Primary Examiner* — Brian P Mruk
(74) *Attorney, Agent, or Firm* — Novak Druce Connolly Bove + Quigg LLP

(57) ABSTRACT

The present invention is directed to a cleansing composition comprising:
(a) at least one nonionic surfactant; (b) at least one amphoteric surfactant; (c) at least one component selected from (i) a nonionic thickener or (ii)(1) a cationic agent combined with (ii)(2) an anionic surfactant, or a mixture of nonionic thickener plus cationic agent and/or anionic surfactant; and (d) water.

17 Claims, No Drawings

VISCOELASTIC CLEANSING GEL

TECHNICAL FIELD

The present invention relates to a viscoelastic cleansing gel composition having a structured phase that may be modified to yield increased or decreased elastic solid behaviors. More particularly, the invention relates to a cleansing composition having a cross over frequency ranging between about 0.1 to about 30 rad/s.

BACKGROUND OF THE INVENTION

Conventional cleansing compositions such as shampoos, for example, contain standard surfactants such as anionic, nonionic and/or amphoteric type surfactants in amounts such that the resulting composition display either liquid or solid rheological behaviors, but not both. Typically such compositions exhibit Newtonian or viscoelastic behavior. Those compositions that exhibit viscoelastic behavior are mostly dominated by liquid behavior within the frequency range 0.1 to 50 rad/s. Solid behavior only becomes dominant at frequencies higher than 50 rad/s and therefore it is not noticeable macroscopically (e.g. by a consumer) under typical usage conditions (e.g. squeezed through the bottle or rubbing between hands).

Conventional shampoos that exhibit gel-like, elastic behaviors typically use structuring agents (also known as thickeners or rheology modifiers) such as saccharides, gums, guars, cellulose derivatives and high molecular weight thickening polymers. See, for example, US Pub. 2004/0097385, U.S. Pat. No. 6,770,607, and U.S. Pat. No. 5,965,502. These materials are known to thicken compositions by building an associative network with other ingredients in the composition (mainly anionic surfactants) resulting in the elastic/solid-like behavior discussed in the foregoing publications. In contrast, the inventive compositions herein disclosed yield cleansing gels that exhibit solid like behavior without the use of rheology modifiers and/or thickeners. It is advantages to avoid such rheology modifiers and thickeners as these materials are known to impact negatively usage qualities of cleansing compositions, such as for example, resulting in slower flash foam, lower overall foam level, lower potential for delivery of actives or conditioning agents, poor distribution during application and slower "break" of the compositions.

The compositions of the invention display liquid behaviors when slowly deformed (e.g. flow freely when the holding container is tilted) and solid, gel-like behaviors when quickly deformed (e.g. touched, sheared or squeezed through and orifice or nozzle). Furthermore these cleansing compositions have Newtonian behavior (that is, nearly ideal liquid behavior) within the range of frequencies where the liquid behavior is dominant and near ideal elastic behavior within the frequency range where the solid behavior is dominant. The compositions of the invention are thus useful in multiple applications of cleaning compositions.

BRIEF SUMMARY OF THE INVENTION

The present invention relates to an aqueous cleansing composition comprising:
 (a) from about 6% to about 20% of at least one nonionic surfactant;
 (b) from about 3% to about 10% of at least one amphoteric surfactant;
 (c) at least one material selected from
  (i) from about 0.1% to about 10% of at least one nonionic thickener; and
  (ii) (1) from about 0.01% to about 5% of at least one cationic agent combined with
   (2) from about 2% to about 8% of an anionic surfactant; and
 (d) from about 40% to about 88% water;
 wherein the amount of the nonionic surfactant a) present in the final composition is greater than the amphoteric surfactant b), and wherein the composition has a crossover frequency of from about 0.1 to about 30 rad/s, the percent amounts being based on the weight percent of each component in the final composition.

The composition may include additional ingredients consistent with its intended use.

The present invention is also directed to a process for cleansing a keratinous substrate, such as hair and skin, involving contacting the keratinous substrate with the above-disclosed cleansing compositions.

These compositions of invention are unusual in that they flow when the container holding them is tilted but exhibit gel-like behavior when touched, sheared or squeezed through an orifice or nozzle.

DETAILED DESCRIPTION OF THE INVENTION

The present compositions result from the finding that an association of a specific amount and ratio of surfactants/agents yields compositions having a structured phase that can be made to behave either as a solid or liquid phase, or in some cases behaviors of both. The compositions are in the form of a structured phase that can be pushed toward the liquid or solid dominant behavior by adjusting the selection or percentage of the key components of the compositions (namely the nonionic thickener ((c)(i)), and/or cationic agent ((c)(ii)(1)), and/or anionic surfactant ((c)(ii)(2)), and mixtures thereof) such as to shift the relaxation time or cross over frequency of the compositions. The resulting structured phase compositions of the invention can be in the form of a rubbery type of gel (also referred to as "snotty" gel), a ringing-vibrating gel, or a harder "crushed ice" gel. Shrinking the domain of the elastic solid phase can reverse the gel texture to a classical liquid-like behavior with a lower degree of or no structured behavior. While many gels display thixotropy (that is, they become fluid when agitated but re-solidify when resting), the compositions of the invention behave somewhat contrary in that they flow evenly and easily when poured from a container but become more solid-like (more gelatinous) when agitated.

Also, unlike currently available compositions that use a gelling agent or high molecular weight thickening polymer to obtain the "jiggling" effect, the instant compositions do not need such high molecular weight polymers, gums, starches or guars, or the association of these materials with anionic surfactants, to obtain this same effect.

It is to be understood that both the foregoing general description and the following detailed description are exemplary and explanatory only, and are not restrictive of the invention.

All percentages and ratios are calculated by weight unless otherwise indicated. All percentages are calculated based on the total composition unless otherwise indicated.

As used herein, all ranges provided are meant to include every specific range within, and combination of sub ranges between, the give ranges. Thus, a range from 1 to 5, includes specifically 1, 2, 3, 4 and 5, as well as 2-5, 3-5, 2-3, 2-4, 1-4, etc.

"About" as used herein means within 10% of the indicated number (e.g. "about 10%" means 9%-11% and "about 2%" means 1.8%-2.2%).

"At least one" as used herein means one or more and thus includes individual components as well as mixtures/combinations.

"Clear" as used herein means that the composition is visually clear. More specifically, clarity of a formulation is measured by the transmittance percentage of light with a wavelength of 700 nm by UV-Visible spectrophotometry. "Clear" samples allow for between 90% and 100% of the light to pass through the formula.

"Cross over frequency" is the frequency at which a composition goes from a liquid dominant behavior to a solid dominant behavior. At the cross over frequency G"/G'=1.

"Delta" is the phase shift between the sinusoidal stress and strain response functions of a material. Delta is always between 0-90.

"Dominating behavior" is used to refer to which modulus dominates the material's response upon exposure to deformation force. If G'>G", the material response is mostly solid like (greater portion of energy is recovered than lost). If G">G', the material response is mostly liquid or viscous (greater portion of energy is dissipated to induce flow).

"Frequency" is the rate at which deformation is applied during oscillatory testing.

G' is known as the elastic storage modulus. It is a measure of the solid behavior of a composition. It characterizes the elastic contribution to the stress response of the material. It is a measurement of energy stored within the material during deformation and recovered after the removal of the force applied.

G" is known as the viscous loss modulus. It is a measure of the liquid behavior of a composition. It characterizes the viscous contribution to the stress response of the material studied. It is a measurement of energy lost or dissipated during deformation. This energy was transformed into a different form such as energy required to set the material in motion and induce flow.

"Gel" and "gel-like" are terms of art. The IUPAC definition is a nonfluid colloidal network or polymer network that is expanded throughout its whole volume by a fluid. Typically, a gel is understood to be a semi-rigid jelly-like colloid in which a liquid is dispersed in a solid.

"Ideal elastic behavior" means that a composition undergoes elastic (reversible) strain when an anisotropic force is applied externally. The energy applied during the strain is stored within the composition and spontaneously triggers a full recovery when the original force is removed.

"Ideal viscous behavior" means a composition undergoes an irreversible strain upon the application of an external force. The energy applied during the strain is transformed and dissipated into a different form such as flowing.

"Keratinous substrates", as used herein, include but are not limited to, skin, hair, lips, eyelashes and nails. A Preferred keratinous substrate is hair.

"Oscillatory testing" is a measurement used to measure the response of materials to applied stress. A force is applied at a certain rate (frequency) and then removed to measure the response of the material being tested.

"Relaxation time" is a function that can be used to interrelate different viscoelastic response functions. This is calculated as the inverse of the oscillatory frequency.

"Structured phase" is a liquid ordered phase or network which interlocks or entangles to form a solid-like matrix that exhibits solid-like behavior.

"Tan delta" is the tangent of the phase angle (delta) between the sinusoidal stress and strain response functions of a material. Tan delta ranges between 0-1. Tan delta between 0.5-1 means dominant liquid-like behavior. Tan delta between 0-0.5 means dominant solid-like behavior.

"Viscoelastic" means that a composition contains both a viscous (liquid) behavior as well as an elastic (solid) behavior. Ideal elastic or viscous behavior is rare. Most materials exhibit both types of behavior depending on the conditions of the forces applied and therefore most materials are classified as viscoelastic.

In an embodiment, the invention relates to a cleansing composition comprising:
(a) at least one nonionic surfactant;
(b) at least one amphoteric surfactant;
(c) at least one material selected from
    (i) at least one nonionic thickener; and
    (ii) (1) at least one cationic agent combined with
        (2) at least one anionic surfactant; and
(d) water;
wherein the amount of the nonionic surfactant a) present in the final composition is greater than the amphoteric surfactant b), and wherein the composition has a cross over frequency of from about 0.1 to about 30 rad/s, the percent amounts being based on the weight percent of each component in the final composition.

In another embodiment, the invention relates to a viscoelastic cleansing composition comprising:
(a) from about 6% to about 20% of at least one nonionic surfactant;
(b) from about 3% to about 10% of at least one amphoteric surfactant;
(c) at least one material selected from
    (i) from about 0.1% to about 10% of at least one nonionic thickener; and
    (ii) (1) from about 0.01% to about 5% of at least one cationic agent combined with
        (2) from about 2% to about 8% of an anionic surfactant; and
(d) from about 40% to about 88% water.
wherein the amount of the nonionic surfactant (a) present in the final composition is greater than the amphoteric surfactant (b), and wherein the composition has a cross over frequency of from about 0.1 rad/s to about 30 rad/s, the percent amounts being based on the weight percent of each component in the final composition.

In another embodiment, the invention relates to a viscoelastic cleansing composition comprising:
(a) from about 6% to about 20% of at least one nonionic surfactant;
(b) from about 3% to about 10% of at least one amphoteric surfactant;
(c) (i) from about 0.1% to about 10% of at least one nonionic thickener; and
(d) from about 40% to about 88% water.
wherein the amount of the nonionic surfactant (a) present in the final composition is greater than the amphoteric surfactant (b), and wherein the composition has a cross over frequency of from about 0.1 rad/s to about 30 rad/s, the percent amounts being based on the weight percent of each component in the final composition.

In another embodiment, the invention relates to a viscoelastic cleansing composition comprising:
(a) from about 6% to about 20% of at least one nonionic surfactant;
(b) from about 3% to about 10% of at least one amphoteric surfactant;

(c) (ii)(1) from about 0.01% to about 5% of at least one cationic agent;
(ii)(2) from about 2% to about 8% of at least one anionic surfactant; and
(d) from about 40% to about 88% water;
wherein the amount of the nonionic surfactant (a) present in the final composition is greater than the amphoteric surfactant (b), and wherein the composition has a cross over frequency of from about 0.1 rad/s to about 30 rad/s, the percent amounts being based on the weight percent of each component in the final composition.

In another embodiment, the invention relates to a viscoelastic cleansing composition comprising:
(a) from about 6% to about 20% of at least one nonionic surfactant;
(b) from about 3% to about 10% of at least one amphoteric surfactant;
(c) (i) from about 0.1% to about 10% of at least one non-ionic thickener;
(c) (ii)(1) from about 0.01% to about 5% of at least one cationic agent; and
(d) from about 40% to about 88% water;
wherein the amount of the nonionic surfactant (a) present in the final composition is greater than the amphoteric surfactant (b), and wherein the composition has a cross over frequency of from about 0.1 rad/s to about 30 rad/s, the percent amounts being based on the weight percent of each component in the final composition.

In another embodiment, the invention relates to a viscoelastic cleansing composition comprising:
(a) from about 6% to about 20% of at least one nonionic surfactant;
(b) from about 3% to about 10% of at least one amphoteric surfactant;
(c) (i) from about 0.1% to about 10% of at least one non-ionic thickener;
(ii)(2) from about 2% to about 8% of at least one anionic surfactant; and
(d) from about 40% to about 88% water;
wherein the amount of the nonionic surfactant (a) present in the final composition is greater than the amphoteric surfactant (b), and wherein the composition has a cross over frequency of from about 0.1 rad/s to about 30 rad/s, the percent amounts being based on the weight percent of each component in the final composition.

In another embodiment, the invention relates to a viscoelastic cleansing composition comprising:
(a) from about 6% to about 20% of at least one nonionic surfactant;
(b) from about 3% to about 10% of at least one amphoteric surfactant;
(c) (i) from about 0.1% to about 10% of at least one non-ionic thickener;
(ii)(1) from about 0.01% to about 5% of at least one cationic agent; and
(ii)(2) from about 2% to about 8% of at least one anionic surfactant; and
(d) from about 40% to about 88% water;
wherein the amount of the nonionic surfactant (a) present in the final composition is greater than the amphoteric surfactant (b), and wherein the composition has a cross over frequency of from about 0.1 rad/s to about 30 rad/s, the percent amounts being based on the weight percent of each component in the final composition.

In another embodiment of the invention the ratio of the amount of (the sum of nonionic surfactant+amphoteric surfactant) to the amount of anionic surfactant is greater than 2:1. This can also be expressed as [(a)+(b)]:(c)(ii)(2)>2:1. Typically this ratio is greater than 3:1, more typically between about 3.5:1 to about 4.5:1, and particularly this ratio is at least 4:1, all based on the weight percent of each component in the final composition.

In another embodiment of the invention the sum of the amount of cationic agent (c)(ii)(1) plus anionic surfactant (c)(ii)(2) is from about 0.01 to about 13. This sum can also be expressed as (c)(ii)(1)+(c)(ii)(2)=from about 0.01 to about 13. Typically this sum is from about 0.5 to about 7.5, based on the weight percent of each component in the final composition.

In another embodiment of the invention the sum of nonionic thickener (c)(i) plus cationic agent (c)(ii)(1) plus anionic surfactant (c)(ii)(2) is from about 0.01 to about 23. This sum can also be expressed as (c)(i)+(c)(ii)(1)+(c)(ii)(2)=from about 0.01 to about 23. Typically this sum is from about 0.5 to about 13, based on the weight percent of each component in the final composition.

In another embodiment the composition has a cross over frequency of from about 2 rad/s to about 25 rad/s, more typically from about 3.2 rad/s to about 22 rad/s.

In another embodiment, at frequencies below the cross over frequency, the inventive compositions have G">G'. The inventive compositions thus have dominating liquid behaviors at rest. Analogously, at frequencies above the cross over frequency, the compositions have G'>G".

Nonionic Surfactants (Component (a))

Non-ionic surfactants, while they are known for good cleaning properties, are not preferred in commercial shampoos in part as they are typically too harsh and drying on keratinous substrates (e.g. hair). However, the ratio of this surfactant to and its association with the amphoteric surfactant of the invention enables the use of non-ionic surfactants in the current cleansing formulation and still yield a conditioning effect.

The at least one nonionic surfactant useful in the cosmetic compositions disclosed herein is selected from: alkyl polyglucosides; ethylene glycol, propylene glycol, glycerol, polyglyceryl esters and their ethoxylated derivatives (herein jointly referred to as "glycol ethers"); as well as amine oxides; and mixtures the foregoing.

Alkyl polyglucosides that may be used in the compositions of the invention include compounds of formula (I)

$$R^1-O-(R^2O)n\text{-}Z(x) \qquad (I)$$

wherein
$R^1$ is an alkyl group having 8-18 carbon atoms;
$R^2$ is an ethylene or propylene group;
Z is a saccharide group with 5 to 6 carbon atoms;
n is an integer from 0 to 10; and
x is an integer from 1 to 5.

Such alkyl polyglucoside compounds include lauryl glucoside, octyl glucoside, decyl glucoside, coco glucoside, sucrose laurate, caprylyl/capryl glucoside, and sodium lauryl glucose carboxylate, and mixtures thereof. Typically, the at least one alkyl poly glucoside compound is selected from the group consisting of lauryl glucoside, decyl glucoside and coco glucoside, and more typically lauryl glucoside.

Non-limiting examples of glycol esters useful in the compositions of the invention include those described in M. R. Porter et al., Handbook of Surfactants, Ch. 7, §7.12, pp. 231-235 ($2^{nd}$ Ed. 1994), which is herein incorporated by reference. Preferred glycol esters have HLB values between about 9 and about 18. Particular glycol esters useful in the compositions of the invention include PEG-8 glyceryl laurate, polysorbate-40, polyglyceryl-5 laurate, and mixtures thereof.

Amine oxides useful in the compositions of the invention include compounds of formulas (IIA) and (IIB)

  (IIA), and

  (IIB)

wherein
R is an alkyl group having 8-18 carbon atoms; and
n is an integer from 1 to 3.

A non-limiting example of a particular amine oxide is laurel amino oxide.

In the present compositions, the at least one nonionic surfactant is used in an amount of from about 6% to about 20%, typically from about 7% to about 10%, and more typically from about 7.1% to about 8%, including all ranges and sub ranges therebetween, by weight based on the total weight of the composition as a whole.

Amphoteric Surfactant (Component (b))

The at least one amphoteric surfactant useful in the cosmetic compositions disclosed herein is chosen from betaines, sultaines, amphoacetates, amphoproprionates, and mixtures thereof. More typically, betaines and amphoproprionates are used, and most typically betaines. Non-limiting examples of betaines useful in the compositions of the invention include those having the following structures XX A-B below

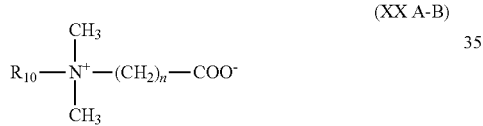  (XX A-B)

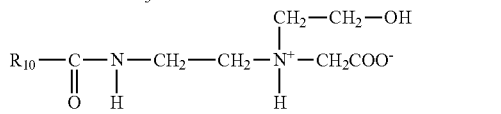

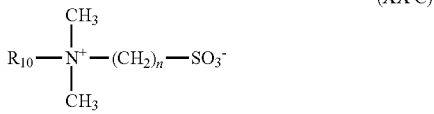  (XX C)

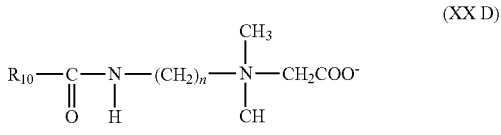  (XX D)

wherein
R10 is an alkyl group having 8-18 carbon atoms; and
n is an integer selected from 1-3.

Particularly useful betaines which can be used in the current compositions include, for example, coco betaine, cocoamidopropyl betaine, lauryl betaine, laurylhydroxy sulfobetaine, lauryldimethyl betaine, cocoamidopropyl hydroxysultaine, behenyl betaine, capryl/capramidopropyl betaine, lauryl hydroxysultaine, stearyl betaine, and mixtures thereof. Typically, the at least one betaine compound is selected from the group consisting of coco betaine, cocoamidopropyl betaine, behenyl betaine, capryl/capramidopropyl betaine, lauryl betaine, and mixtures thereof, and more typically cocoamidopropyl betaine.

Hydroxyl sultaines useful in the compositions of the invention include the following

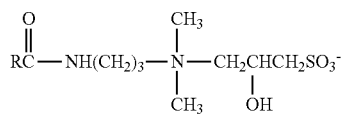  (XXIII)

wherein
R is an alkyl group having 8-18 carbon atoms.

Useful alkylamphoacetates include those having the formula (XXIV)

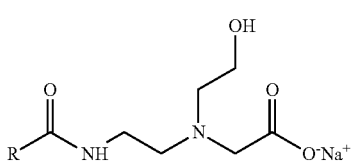  (XXIV)

wherein
R is an alkyl group having 8-18 carbon atoms.

Useful alkyl amphodiacetates include those having the formula (XXV)

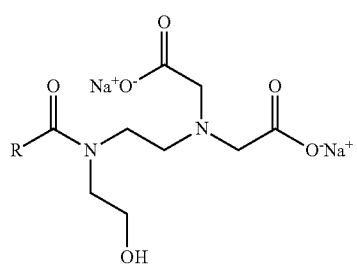  (XXV)

wherein
R is an alkyl group having 8-18 carbon atoms.

Useful amphoproprionates include sodium cocoamphopropionate.

In an embodiment, the at least one amphoteric surfactant (b) is selected from the group consisting of coco betaine, cocoamidopropyl betaine, sodium behenyl betaine, capryl/capramidopropyl betaine, lauryl betaine, sodium cocamphopropionate and mixtures thereof, and more typically cocoamidopropyl betaine, cocobetaine and sodium cocamphopropionate, and mixtures thereof.

In the present compositions, the at least one amphoteric surfactant (b) is used in an amount of from about 3% to about 10% by weight, typically from about 4% to about 8% by weight, and more typically from about 5% to about 6% by weight, including all ranges and sub ranges therebetween, based on the total weight of the composition as a whole.

Nonionic Thickener (Component (c)(i))

Non-limiting examples of nonionic thickeners that may be used in the compositions of the invention include low molecular weight compounds of formula (III)

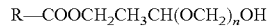  (III)

wherein
R is $C_8$-$C_{22}$ alkylene
n is from 1 to 1000.

Non-limiting examples of compounds of formula (III) include those in the table below:

| USA INCI name | Commercial reference | Supplier |
|---|---|---|
| PROPYLENE GLYCOL (and) PEG-55 PROPYLENE GLYCOL OLEATE | ANTIL 141 LIQUID | EVONIK GOLDSCHMIDT |
| PEG-7 GLYCERYL COCOATE | GLYCEROX HE | CRODA |
| peg/ppg-8/3 laurate | HYDRAMOL PGPL ESTER | LUBRIZOL |
| PEG-10 OLEATE | EMALEX OE-10 | NIHON EMULSION |
| PEG-30 GLYCERYL COCOATE | REWODERM LI 63 | EVONIK GOLDSCHMIDT |
| PEG-32 STEARATE | STEARATE 1540 | GATTEFOSSE |
| PEG-12 LAURATE | EMANON 1112 | KAO |
| PEG-8 ISOSTEARATE | CITHROL 4MIS-LQ-(GD) | CRODA |
| PEG-55 STEARATE | NIKKOL MYS-55V | NIKKO CHEMICALS |

In addition, the PEG mono- and di-esters of the compounds of formula (III) are also useful in the invention. These compounds have the following structures:

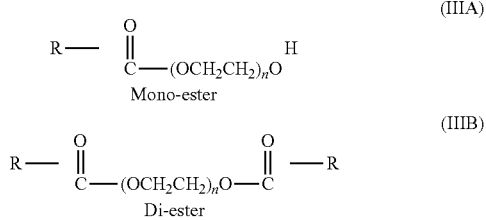

$$R-\overset{O}{\underset{\|}{C}}-(OCH_2CH_2)_nO-H \quad \text{(IIIA)}$$

Mono-ester $$R-\overset{O}{\underset{\|}{C}}-(OCH_2CH_2)_nO-\overset{O}{\underset{\|}{C}}-R \quad \text{(IIIB)}$$

Di-ester wherein R and n are as defined above.

Non-limiting examples of these compounds include the compounds in the table below.

| USA INCI name | Commercial reference | Supplier |
|---|---|---|
| PEG-7 GLYCERYL COCOATE | GLYCEROX HE | CRODA |
| peg/ppg-8/3 laurate | HYDRAMOL PGPL ESTER | LUBRIZOL |
| PEG-10 OLEATE | EMALEX OE-10 | NIHON EMULSION |
| PEG-8 DISTEARATE | DISTEARATE DE PEG 400 (DUB DS PEG 8) | STEARINERIE DUBOIS |
| PEG-150 DISTEARATE | LIPO PEG. 6000 DS | LIPO CHEMICALS |
| PEG-4 DIHEPTANOATE | LIPONATE 2DH | LIPO CHEMICALS |
| PEG-20 METHYL GLUCOSE DISTEARATE | GLUCAM E 20 DISTEARATE | AMERCHOL (DOW CHEMICAL) |
| PEG/PPG-8/3 DIISOSTEARATE | HYDRAMOL PGPD | NOVEON EUROPE BVBA |
| PEG-30 GLYCERYL COCOATE | REWODERM LI 63 | EVONIK GOLDSCHMIDT |
| PEG-32 STEARATE | STEARATE 1540 | GATTEFOSSE |
| PEG-12 LAURATE | EMANON 1112 | KAO |
| PEG-8 ISOSTEARATE | CITHROL 4MIS-LQ-(GD) | CRODA |
| PEG-55 STEARATE | NIKKOL MYS-55V | NIKKO CHEMICALS |

The nonionic thickener can alternatively have formula (IV) as follows

$$H(OCH_2CH_2)_nOH \quad \text{(IV)}$$

wherein n is from 1 to 1000.

Non-limiting examples of these compounds are provided in the table below.

| USA INCI name | Trade Name | Supplier |
|---|---|---|
| PEG-32 | PLURACARE E 1500 | BASF |
| PEG-8 | PLURACARE E 400 | BASF |
| PEG-20 | CARBOWAX SENTRY POLYETHYLENE GLYCOL 1000 NF, FCC GRADE | DOW CHEMICAL |
| PEG-180 | POLYGLYKOL 8000 S | CLARIANT |
| | CARBOWAX SENTRY POLYETHYLENE GLYCOL 8000 NF FCC FLAKE | DOW CHEMICAL |
| | K-PEG 180 | KAO |

When referencing the thickener, "low molecular weight" herein means that the repeating unit "n" in the above formulas is equal to or less than 1000. In preferred embodiments, n in each of the above formulas is less than 500, preferably less than 200.

In a particular embodiment, the nonionic thickener is selected from PEG-55 propylene glycol oleate, propylene glycol (and) PEG-55 propylene glycol oleate, PEG-8 and mixtures thereof.

The at least one nonionic thickener (c)(i) is present in a total amount ranging from about 0.1% to about 10% by weight, typically from about 0.25% to about 8%, more typically from about 0.3% to about 5% by weight, including all ranges and sub ranges therebetween, based on the total weight of the composition as a whole.

Cationic Agent (Component (c)(ii)(1))

The at least one cationic agent used in the compositions disclosed herein is chosen, for example, from cationic polymers, including homopolymers and copolymers, cationic surfactants, cationic amines, cationic amino silicones and cationic silanes. All of these agents are preferably also conditioning cationic agents. These agents are not known in the art as being rheology modifiers or structure building/gelling agents.

Non-limiting examples of polymers that can be used in the current compositions include: cationic cellulose derivatives, such as for example polyquaternium-10 ("PQ-10"); cationic gum derivatives such as for example gum derivatives, including particularly guar hydroxypropyltrimonium chloride; polymer derivatives of diallyldimethyl ammonium chloride ("poly-DADMAs") and of methacrylamidopropyltrimethylammonium chloride ("poly-MAPTACs"), such as for example, polyquaternium-4 (PQ-4), polyquaternium-5 (PQ-5), polyquaternium-6 (PQ-6), polyquaternium-7 (PQ-7), polyquaternium-22 (PQ-22), polyquaternium-37 (PQ-37), polyquaternium-39 (PQ-39), polyquaternium47 (PQ-47) and polyquaternium-53 (PQ-53), particularly DADMAC-based polymers, specifically PQ-6 and PQ-22; and cationic proteins, such as, for example, hydroxypropyltrimonium hydrolyzed wheat protein.

By "DADMAC-based polymers" applicants' mean polymers including the following chemical group.

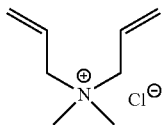

In a particular embodiment, the cationic polymer is selected from PQ-6, PQ-22, and mixtures thereof.

Cationic Surfactant and Cationic Amines

The cationic surfactant useful in the cosmetic compositions disclosed herein optionally is selected from mono and di-alkyl quaternary ammonium or diammonium salts.

By way of example only, quaternary ammonium or diammonium salts described in US2005071933, incorporated by reference herein, may be chosen, such as, for example, those of the general formula (VA):

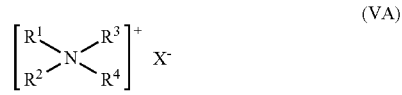

wherein, in formula (VA):
$R^1$ and $R^4$, may independently be chosen from saturated or unsaturated, linear or branched, aliphatic hydrocarbon radicals comprising from 1 to about 30 carbon atoms, or an alkoxy, alkoxycarbonylalkyl, polyoxyalkylene, alkylamido, alkylamidoalkyl, hydroxyalkyl, aromatic, aryl or alkylaryl radical comprising from about 12 to about 30 carbon atoms, with at least one radical among $R^1$, $R^2$, $R^3$ and $R^4$ denoting a radical comprising from 8 to 30 carbon atoms; and
$X^-$ is an anion chosen from the group comprising halides, phosphates, acetates, lactates and alkyl sulfates;
and/or general formula (VB):

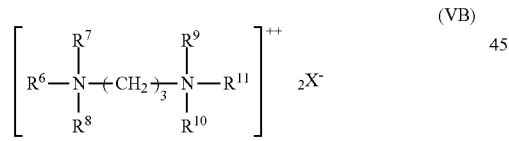

wherein, in formula (VB):
$R^6$ denotes an aliphatic radical comprising from about 16 to 30 carbon atoms,
$R^7$, $R^8$, $R^9$, $R^{10}$ and $R^{11}$ are independently chosen from hydrogen or an alkyl radical comprising from 1 to 4 carbon atoms, and
$X^-$ is an anion chosen from the group comprising halides, acetates, phosphates and sulfates Quaternary ammonium and diammonium salts include, for example, distearyldimethylammonium chloride, cetyltrimethylammonium chloride ("CATC"), behenyltrimethylammonium chloride, behentrimonium chloride, cetrimonium chloride oleocetyldimethylhydroxyethylammonium chloride, stearamidopropyldimethyl (myristyl acetate) ammonium chloride, di($C_1$-$C_2$ alkyl) ($C_{12}$-$C_{22}$ alkyl)hydroxy($C_1$-$C_2$ alkyl)ammonium salt, such as dialkyldimethylammonium or alkyltrimethylammonium salt in which the alkyl radical preferably comprises 12 to 24 carbon atoms, propanetallowdiammonium dichloride, behentrimonium methosulfate, and mixtures thereof.

Non-limiting examples of particular quaternary ammonium salts that can be used in the current compositions include in particular cetyltrimethylammonium chloride, behentrimonium chloride, cetrimonium chloride, behentrimonium methosulfate, and mixtures thereof.

Non-limiting examples of cationic amines that can be used in the current compositions include dimethylamine derivatives, such as for example stearyl dimethyl amine, stearamidopropyl dimethylamine, brassicamidopropyl dimethylamine, and mixtures thereof.

In an embodiment the cationic agent is selected from stearamidipropyl dimethylamine, cetrimonium chloride, behentrimonium chloride, and mixtures thereof.

Amino Silicones and Silanes

The term "amino silicone" means any polyaminosiloxane, i.e. any polysiloxane comprising at least one primary, secondary or tertiary amine function or a quaternary ammonium group. Preferably, the amino silicone(s) used in the cosmetic composition according to the present invention are selected from (A)-(D) as described below.

Amino silicones are described, for example, in US2011/0155163 and US2011/155164, both of which are herein incorporated by reference.

Compounds corresponding to formula (VI)

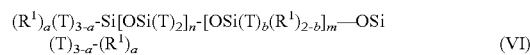

wherein
T is a hydrogen atom or a phenyl, hydroxyl (—OH) or $C_1$-$C_2$ alkyl radical, and preferably methyl, or a $C_1$-$C_8$ alkoxy, preferably methoxy,
a denotes the number 0 or an integer from 1 to 3, and preferably 0,
b denotes 0 or 1, and in particular 1,
m and n are numbers such that the sum (n+m) can range especially from 1 to 2000 and in particular from 50 to 150, it being possible for n to denote a number from 0 to 1999 and in particular from 49 to 149, and for m to denote a number from 1 to 2000 and in particular from 1 to 10;
$R^1$ is a monovalent radical of formula —$C_qH_{2q}L$ in which q is a number from 2 to 8 and L is an optionally quaternized amino group selected from the following groups:

—N($R^2$)—$CH_2$—$CH_2$—N($R^2$)$_2$;
—N($R^2$)$_2$; —$N^+$($R^2$)$_3$$Q^-$;
—$N^+$($R^2$)(H)$_2$$Q^-$;
—$N^+$($R^2$)$_2$H$Q^-$;
—N($R^2$)—$CH_2$—$CH_2$—$N^+$($R^2$)(H)$_2$$Q^-$, in which $R^2$ denotes a hydrogen atom, a phenyl, a benzyl or a saturated monovalent hydrocarbon-based radical, for example a $C_1$-$C_{20}$ alkyl radical, and $Q^-$ represents a halide ion, for instance fluoride, chloride, bromide or iodide.

In particular, the amino silicones corresponding to the definition of formula (VI) are selected from the compounds corresponding to formula (VIA) below:

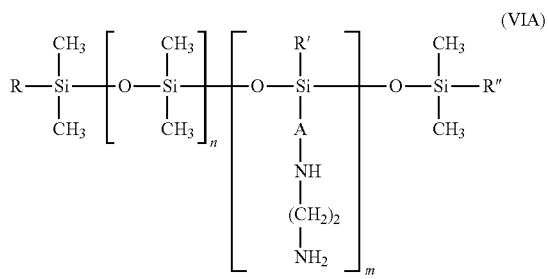

in which R, R' and R", which may be identical or different, denote a $C_1$-$C_4$ alkyl radical, preferably $CH_3$; a $C_1$-$C_4$ alkoxy radical, preferably methoxy; or OH; A represents a linear or branched, $C_3$-$C_8$ and preferably $C_3$-$C_6$ alkylene radical; m and n are integers dependent on the molecular weight and whose sum is between 1 and 2000.

According to a first possibility, R, R', R", which may be identical or different, represent a $C_1$-$C_4$ alkyl or hydroxyl radical, A represents a $C_3$ alkylene radical and m and n are such that the weight-average molecular weight of the compound is between 5000 and 500 000 approximately. Compounds of this type are referred to in the CTFA dictionary as "aminodimethicones".

According to a second possibility, R, R' and R", which may be identical or different, represent a $C_1$-$C_4$ alkoxy or hydroxyl radical, at least one of the radicals R or R" is an alkoxy radical and A represents a $C_3$ alkylene radical. The hydroxy/alkoxy molar ratio is preferably between 0.2/1 and 0.4/1 and advantageously equal to 0.3/1. Moreover, m and n are such that the weight-average molecular weight of the compound is between 2000 and $10^6$. More particularly, n is between 0 and 999 and m is between 1 and 1000, the sum of n and m being between 1 and 1000.

In this category of compounds, mention may be made, inter alia, of the product BELSIL® ADM 652 sold by Wacker.

According to a third possibility, R and R", which are different, represent a $C_1$-$C_4$ alkoxy or hydroxyl radical, at least one of the radicals R or R" is an alkoxy radical, R' represents a methyl radical and A represents a $C_3$ alkylene radical. The hydroxy/alkoxy molar ratio is preferably between 1/0.8 and 1/1.1 and advantageously equal to 1/0.95. Moreover, m and n are such that the weight-average molecular weight of the compound is between 2000 and 200 000. More particularly, n is between 0 and 999 and m is between 1 and 1000, the sum of n and m being between 1 and 1000.

More particularly, mention may be made of the product FLUID WR® 1300 sold by Wacker.

According to a fourth possibility, R and R" represent a hydroxyl radical, R' represents a methyl radical and A is a $C_4$-$C_8$ and preferably $C_4$ alkylene radical. Moreover, m and n are such that the weight-average molecular weight of the compound is between 2000 and $10^6$. More particularly, n is between 0 and 1999 and m is between 1 and 2000, the sum of n and m being between 1 and 2000.

A product of this type is especially sold under the name DC 28299 by Dow Corning.

The molecular weight of these silicones is determined by gel permeation chromatography (ambient temperature, polystyrene standard; μ styragem columns; eluent THF; flow rate 1 mm/m; 200 μl of a solution containing 0.5% by weight of silicone in THF are injected, and detection is performed using a refractometer and a UV meter).

A particular product of formula (VIA) is the polymer known in the CTFA dictionary (7th edition, 1997) as "trimethylsilylamodimethicone", corresponding to formula (VIB)

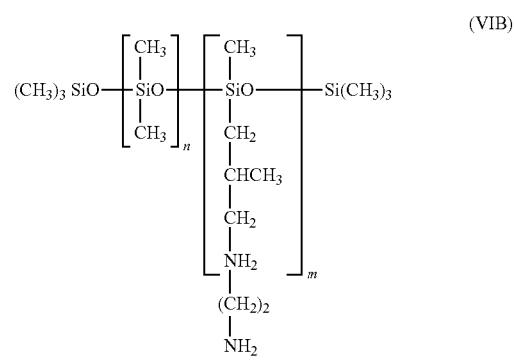

in which n and m have the meanings given above in accordance with formula (VI) or (VIA) above.

Such compounds are described, for example, in EP 0 095 238, which is herein incorporated by reference. A compound of formula (VIB) is sold, for example, under the name Q2-8220 by the company OSI.

(B) The second type of amino silicone compounds correspond to formula (VII)

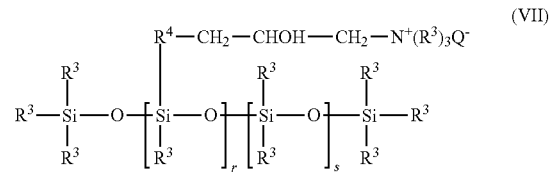

in which:
$R^3$ represents a $C_1$-$C_{18}$ monovalent hydrocarbon-based radical, and in particular a $C_1$-$C_{18}$ alkyl or $C_2$-$C_{18}$ alkenyl radical, for example methyl;
$R^4$ represents a divalent hydrocarbon-based radical, especially a $C_1$-$C_{18}$ alkylene radical or a divalent $C_1$-$C_{18}$, and for example $C_1$-$C_8$, alkylenoxy radical;
$Q^-$ is a halide ion, in particular chloride;
r represents a mean statistical value from 2 to 20 and in particular from 2 to 8;
s represents a mean statistical value from 20 to 200 and in particular from 20 to 50.

Such compounds are described more particularly in U.S. Pat. No. 4,185,087, which is herein incorporated by reference.

A compound falling within this class is the product sold by the company Union Carbide under the name Ucar Silicone ALE 56.

(C) Quaternary ammonium silicones of formula (VIII) are another type of silicone useful in the invention:

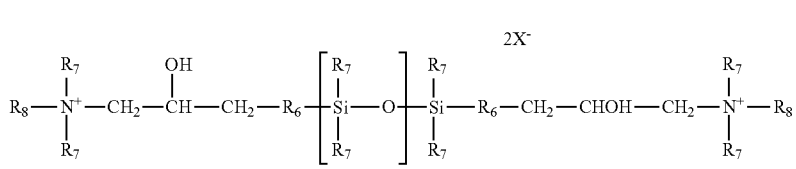

(VIII)

in which:
- $R_7$, which may be identical or different, represent a monovalent hydrocarbon-based radical containing from 1 to 18 carbon atoms, and in particular a $C_1$-$C_{18}$ alkyl radical, a $C_2$-$C_{18}$ alkenyl radical or a ring comprising 5 or 6 carbon atoms, for example methyl;
- $R_6$ represents a divalent hydrocarbon-based radical, especially a $C_1$-$C_{18}$ alkylene radical or a divalent $C_1$-$C_{18}$, and for example $C_1$-$C_8$, alkylenoxy radical linked to the Si via an SiC bond;
- $R_8$, which may be identical or different, represent a hydrogen atom, a monovalent hydrocarbon-based radical containing from 1 to 18 carbon atoms, and in particular a $C_1$-$C_{18}$ alkyl radical, a $C_2$-$C_{18}$ alkenyl radical or a radical —$R_6$—$NHCOR_7$;
- $X^-$ is an anion such as a halide ion, especially chloride, or an organic acid salt (acetate, etc.); and r represents a mean statistical value from 2 to 200 and in particular from 5 to 100.

These silicones are described, for example, in patent application EP-A 0 530 974, which is herein incorporated by reference.

An example of the compound of formula (VIII) is the product referenced in the CTFA dictionary (1997 edition) as Quaternium 80. Such a product is marketed by the company Evonik Goldschmidt under the names ABIL QUAT 3272 or 3474.

(D) Formula (IX) below provides another example of amino silicones useful in the invention:

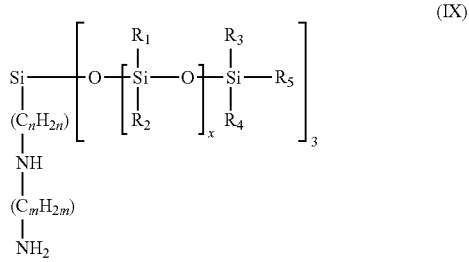

(IX)

in which:
$R_1$, $R_2$, $R_3$ and $R_4$, which may be identical or different, denote a $C_1$-$C_4$ alkyl radical or a phenyl group,
$R_5$ denotes a $C_1$-$C_4$ alkyl radical or a hydroxyl group,
n is an integer ranging from 1 to 5,
m is an integer ranging from 1 to 5,
and in which x is selected such that the amine number is between 0.01 and 1 meq/g.

Amino silicone(s) that are particularly useful in the invention include polysiloxanes containing amine groups, such as the compounds of formula (VIA) or of formula (VI), and even more particularly the silicones containing quaternary ammonium groups of formula (VIII).

Non-limiting examples of particularly useful silicones include aminodimethicones, such as the products available from the company Wacker under the name FLUID® (for example FLUID® WR 1300) and BELSIL® (for example BELSIL® ADM652). Also useful is trimethylsilylaminodimethicone (such as Q@-8220 available from OSI).

Silane Compounds

Exemplary silanes that may be used according to various embodiments of the disclosure include, but are not limited to, organosilanes and derivatives thereof, such as alkylsilanes, allylsilanes, and alkoxysilanes.

In various exemplary embodiments, the at least one silane compound may be chosen from alkoxysilanes comprising at least one solubilizing functional group, such as for example, methoxysilanes, triethoxysilanes, aminopropyltriethoxysilane, methyltriethoxysilane, and derivatives thereof and mixtures thereof.

As used herein, the term "at least one solubilizing functional group" means any functional chemical group facilitating the bringing into solution of the alkoxysilane in the solvent or in a combination of solvents of the composition, for example, in solvents chosen from water, water-alcoholic mixtures, organic solvents, polar solvents and non-polar solvents. Suitable solubilizing functional groups include, but are not limited to, primary, secondary, and tertiary amine, aromatic amine, alcohol, carboxylic acid, sulfonic acid, anhydride, carbamate, urea, guanidine, aldehyde, ester, amide, epoxy, pyrrole, dihydroimidazole, gluconamide, pyridyle, and polyether groups.

In an embodiment the at least one alkoxysilane comprising at least one solubilizing functional group may comprise two or three alkoxy functions. In another embodiment, the alkoxy functional groups are chosen from methoxy and ethoxy functional groups.

According to a further embodiment, the at least one alkoxysilane comprising at least one solubilizing functional group present in the composition of the present disclosure is chosen from compounds of formula (X):

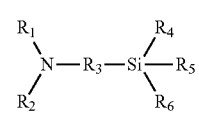

(X)

wherein,
$R_4$ is chosen from halogen atoms, OR' groups, and $R_{11}$ groups;
$R_5$ is chosen from halogen atoms, OR" groups, and $R_{12}$ groups;
$R_6$ is chosen from halogen atoms, OR''' groups, and $R_{13}$ groups;

$R_1$, $R_2$, $R_3$, R', R", R''', $R_{11}$, $R_{12}$, and $R_{13}$, which may be identical or different, are chosen from linear and branched, saturated and unsaturated hydrocarbon groups, optionally bearing at least one additional chemical group, wherein $R_1$, $R_2$, R', R", and R''' may also be chosen from hydrogen;

provided that at least two groups $R_4$, $R_5$, and $R_6$ are different from $R_{11}$, $R_{12}$, and $R_{13}$, and at least two groups R', R", and R''' are not hydrogen.

The at least one alkoxysilane comprising at least one solubilizing functional group may also be chosen from compounds of formula (XA):

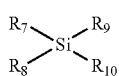

wherein, $R_9$ is chosen from halogen atoms and OR'$_9$ groups;

$R_{10}$ is chosen from halogen atoms and OR'$_{10}$ groups;

R'$_9$ and R'$_{10}$, which may be identical or different, are chosen from hydrogen, and linear and branched, saturated and unsaturated $C_1$-$C_{14}$ hydrocarbon groups;

$R_7$ is a non hydrolyzable functional group providing a cosmetic effect; and $R_8$ is a non hydrolyzable functional group bearing at least one function chosen from amines, carboxylic acids and salts thereof, sulfonic acids and salts thereof, polyols such as glycol, polyethers such as polyalkylene ether, and phosphoric acids and salts thereof; and provided that at least one of $R_9$ and $R_{10}$ is not a halogen;

As used herein, the term "functional group providing a cosmetic effect" means a group derived from an entity chosen from reducing agents, oxidizing agents, coloring agents, polymers, surfactants, antibacterial agents, and UV absorbing filters.

According to a third embodiment, the at least one alkoxysilane comprising at least one solubilizing functional group may be chosen from compounds of formula (XB):

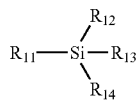

wherein, $R_{12}$ is chosen from halogen atoms, OR'$_{12}$ groups, and $R_o$ groups;

$R_{13}$ is chosen from halogen atoms, OR'$_{13}$ groups, and R'$_o$ groups;

$R_{14}$ is chosen from halogen atoms, OR'$_{14}$ groups, and R"$_o$ groups;

$R_{11}$ is chosen from groups bearing at least one function chosen from carboxylic acids and salts thereof, sulfonic acids and salts thereof, and polyalkylethers;

Ro, R'o, R"o, R'$_{12}$, R'$_{13}$, and R'$_{14}$, which may be identical or different, are chosen from linear and branched, saturated and unsaturated, $C_1$-$C_{14}$ hydrocarbon groups optionally bearing at least one additional chemical functional group chosen from carboxylic acids and salts thereof, sulfonic acids and salts thereof, and polyalkylether functions, and wherein R'$_{12}$, R'$_{13}$, and $R_{14}$ may also be chosen from hydrogen;

provided that at least two groups from $R_{12}$, $R_{13}$ and $R_{14}$ are different from $R_o$, R'$_o$, and R"$_o$ groups; and provided further that at least two of the groups R'$_{12}$, R'$_{13}$, and R'$_{14}$ are not hydrogen.

According to another embodiment, the at least one alkoxysilane comprising at least one solubilizing functional group may be chosen from compounds of formula (XI):

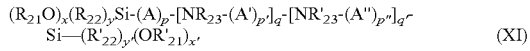

wherein, $R_{21}$, $R_{22}$, R'$_{21}$, and R'$_{22}$, which may be identical or different, are chosen from linear and branched, saturated and unsaturated hydrocarbon chains, optionally comprising at least one heteroatom, optionally interrupted by or substituted with at least one group chosen from ether, ester, amine, amide, carboxyl, hydroxyl, and carbonyl groups;

x is an integer ranging from 1 to 3;

y is 3-x;

x' is an integer ranging from 1 to 3;

y' is 3-x', p, p', p", q, and q' can each be 0 or 1, wherein at least one of q or q' is not equal to zero;

A, A', and A", which may be identical or different, are chosen from linear and branched $C_1$-$C_{20}$ alkylene divalent radicals; and $R_{23}$ and R'$_{23}$, which may be identical or different, are chosen from hydrogen and linear and branched, saturated and unsaturated hydrocarbon chains, optionally comprising at least one heteroatom, optionally interrupted by or substituted with at least one entity chosen from ether, $C_1$-$C_{20}$ alcohol ester, amine, carboxyl, alkoxysilane, $C_6$-$C_{30}$ aryl, hydroxyl, and carbonyl groups, and aromatic, heterocyclic, and non-heterocyclic rings, optionally substituted with at least one group chosen from $C_3$-$C_{20}$ alcohol ester, amine, amide, carboxyl, alkoxysilane, hydroxyl, carbonyl, and acyl groups.

The at least one alkoxysilane comprising at least one solubilizing functional group may also be chosen from compounds of formula (XII):

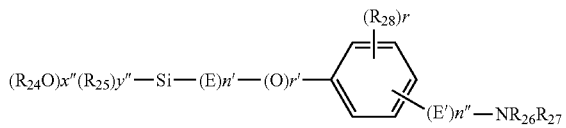

wherein, $R_{24}$ and $R_{25}$, which may be identical or different, are chosen from linear and branched, saturated and unsaturated hydrocarbon chains, optionally comprising at least one heteroatom, optionally interrupted by or substituted with at least one group chosen from ether, ester, amine, amide, carboxyl, hydroxyl, and carbonyl groups;

x" is 2 or 3;

y" is 3-x";

n' is 0 or 1;

n" is 0 or 1;

E and E', which may be identical or different, are chosen from linear and branched $C_1$-$C_{20}$ alkylene divalent radicals;

$R_{26}$ and $R_{27}$, which may be identical or different, are chosen from hydrogen and linear and branched, saturated and unsaturated hydrocarbon chains, optionally comprising at least one heteroatom, optionally interrupted by or substituted with at least one entity chosen from ether, $C_1$-$C_{20}$ alcohol ester, amine, carboxyl, alkoxysilane, $C_6$-$C_{30}$ aryl, hydroxyl, and carbonyl groups, and aromatic, heterocyclic, and non-heterocyclic rings, optionally substituted with at least one group chosen from $C_1$-$C_{20}$ alcohol ester, amine, amide, carboxyl, alkoxysilane, hydroxyl, carbonyl, and acyl groups;

r is an integer ranging from 0 to 4;

r'=0 or 1; and $R_{28}$ is chosen from hydrogen and linear and branched, saturated and unsaturated hydrocarbon chains, comprising, optionally at least one heteroatom, optionally interrupted by or substituted with at least one entity chosen from ether, alkyl alcohol ester, amine, carboxyl, alkoxysilane, alkyl aryl, hydroxyl, and carbonyl groups, and aromatic, heterocyclic, and non-heterocyclic rings.

According to a further exemplary embodiment, the at least one alkoxysilane comprising at least one solubilizing functional group may be chosen from compounds of formula (XIII):

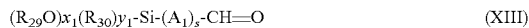

wherein, $R_{29}$ and $R_{30}$, independently, are chosen from linear and branched, saturated and unsaturated hydrocarbon chains, optionally comprising at least one heteroatom, optionally interrupted by or substituted with at least one group chosen from ether, ester, amine, amide, carboxyl, hydroxyl, and carbonyl groups;

$x_1$ is 2 or 3;

$y_1$ is 3-$x_1$;

$A_1$ is chosen from linear and branched $C_1$-$C_{20}$ alkylene divalent radicals, optionally interrupted by or substituted with at least one group chosen from $C_1$-$C_{30}$ alcohol ester, amine, carboxyl, alkoxysilane, $C_6$-$C_{30}$ aryl, hydroxyl, and carbonyl groups; and s is 0 or 1.

In a further exemplary embodiment, the at least one alkoxysilane comprising at least one solubilizing functional group is chosen from compounds of formula (XIV):

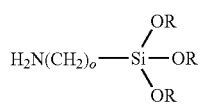

wherein the R radicals, which may be identical or different, are chosen from $C_1$-$C_6$ alkyl radicals and n is an integer ranging from 1 to 6, for example, from 2 to 4.

The alkoxysilanes useful in the present disclosure can be chosen from alkoxysilanes comprising a silicon atom in a formula $R_{(4-n)}SiX_n$, wherein X is a hydrolysable group such as methoxy, ethoxy or 2-methoxyethoxy, R is a monovalent organic radical which contains 1 to 12 carbon atoms and may contain groups such as mercapto, epoxy, acrylyl, methacrylyl, amino or urea, and n is an integer from 1 to 4, and according to at least one embodiment is 3. Exemplary alkoxysilanes include, but are not limited to, 3-mercaptopropyltriethoxysilane and aminoalkyltrialkoxysilanes such as 3-aminopropyltriethoxysilane, as described in French Patent Application No. FR2789896, incorporated by reference herein.

Other useful alkoxysilanes are cited, for example, in EP1216022, incorporated by reference herein, which describes alkoxysilanes comprising at least one hydrocarbon chain containing a non-basic solubilizing chemical function. In this respect, non-limiting mention may be made of the HCl— neutralized sodium N-[(3-trimethoxysilyl)propyl]ethylenediaminetriacetate supplied by GELEST.

In an embodiment, the alkoxysilanes may comprise at least one hydrocarbon chain containing fluorine atoms. Possible examples include but are not limited to the 3,3,3-trifluoropropyltriethoxysilane or tridecafluorooctyltriethoxysilane compounds described in EP1510197, incorporated by reference herein.

In another embodiment, the useful alkoxysilanes may be alkoxysilanes that carry a group having a cosmetic functional group. Such cosmetic functional group can be an aromatic nitro dye or anthraquinone, napthoquinone, benzoquinone, azo, xanthene, triarylmethane, azine, indoaniline, indophenolic or indoamine dye.

Another cosmetic functional group is a group having a reductive effect, such as thiol groups, sulphinic acid or sulphinic salt.

It is also contemplated that these alkoxysilanes may carry a solubilizing, non-hydrolysable group such as amino groups, carboxylic acids, sulphonic acids, sulphates, quaternary ammoniums, polyalcohols, polyether and phosphates. One possible example of the foregoing types of alkoxysilanes is aminopropyl-N-(4,2-dinitrophenyl)aminopropyldiethoxysilane. Additional exemplary compounds of this type are described, for example, in EP1216023, which is herein incorporated by reference.

Non-limiting examples of useful alkoxysilanes include 3-mercaptopropyltriethoxysilane and aminoalkyltrialkoxysilanes such as 3-aminopropyltriethoxysilane ("APTES", described in French Patent Application No. FR 2 789 896, incorporated herein by reference), and mixtures thereof.

In an embodiment cationic agent (c)(ii)(1) is selected from polyquaternium-6 (PQ-6), polyquaternium-22 (PQ-22), cetyltrymethyl ammonium chloride (CTAC), and mixtures thereof.

The at least one cationic agent (c)(ii)(1) is present in the compositions of the invention in an amount of from about 0.01% to about 5% by weight, typically from about 0.1% to about 3% by weight, and more typically from about 0.25% to about 2%, by weight, based on the total weight of the composition as a whole. In a particular embodiment, the amount of cationic conditioning polymer is present at about 1% by weight, based on the total weight of the composition as a whole.

Anionic Surfactant (Component (c)(ii)(2))

The at least one anionic surfactant used in the cosmetic compositions disclosed herein can be, for example, chosen from salts, for example, alkali metal salts such as sodium salts, ammonium salts, amine salts, amino alcohol salts and alkaline-earth metal salts, for example magnesium salts, of the following types of compounds: alkyl sulfates, alkyl ether sulfates, acyl isethionates, acyl glycianates, acyl taurates, acyl amino acids, acyl sarcosinates, sulfosuccinates, sulfonates, alkyl polyglucoside sulfonates and alkyl polyglucoside carboxylates, the alkyl and acyl groups of all these compounds comprising from 6 to 24 carbon atoms (saturated or unsaturated, linear or branched).

Particular sulfate salts useful in the invention include those having the formulas (XXVI A and B)

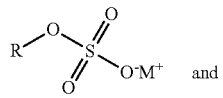 (XXVI A)

and

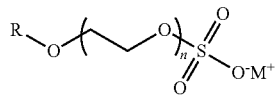 (XXVIB)

wherein
R is alkyl chain having 6 to 24 carbon atoms;
M is an alkali-metal salt as described above; and
n is from 0 to 3 moles.
Non-limiting examples of acyl amino acids, taurates, isethionate, sulfosuccinates and sulfonates useful in the compositions of the invention include those having the following formulas:

Acyl amino acids:

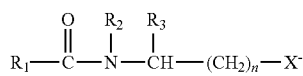 (XXVII)

Taurates:

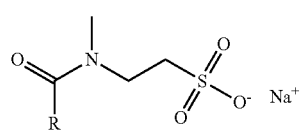 (XXVIII)

Isethionate:

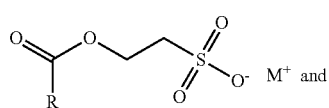 (XXIX A)

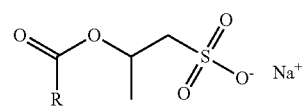 (XXIX B)

Sulfosuccinates:

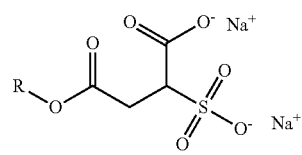 (XXX)

Sulfonates:

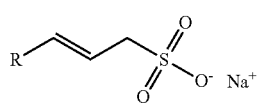 (XXXI)

wherein in the above formulas R, $R^1$, $R^2$ and $R^3$ are each independently selected from H or alkyl chain that has 1-24 carbon atoms, said chain being saturated or unsaturated, linear or branched, and X is COO— or $SO_3$—.
Non-limiting examples of alkyl ether sulfates that can be used in the current compositions include lauryl sulfate, laureth sulfate, and salts and mixtures of these. More particularly, the lauryl sulfate is sodium lauryl sulfate and the laureth sulfate is sodium laureth sulfate ("SLES").

Non-limiting examples of isethionates that can be used in the current compositions include sodium cocoyl isethionate, sodium lauroyl methyl isethionate, and mixtures thereof.

A non-limiting example of a glycinate that can be used in the current compositions is sodium cocoyl glycinate.

Non-limiting examples of taurates that can be used in the current compositions are sodium cocoyl taurate and sodium methyl cocoyl taurate.

Acyl amino acids that can be used in the current compositions include amino acid surfactants based on glycine or alanine. The salt ion attached to the at least one acyl amino acid can be sodium or potassium. Examples of acyl amino acid compounds include but are not limited to: sodium cocoyl glycinate, potassium cocoyl glycinate, and sodium lauryl sarcosinate, sodium cocoyl alaninate, sodium cocoyl alanine, and salts thereof. Typically, the at least one acyl amino acid is selected from the group consisting of sodium cocoyl glycinate and potassium cocoyl glycinate, and in particular sodium cocoyl glycinate.

A non-limiting example of a sulfosuccinate that can be used in the current compositions is disodium laurel sulfosuccinate.

A non-limiting example of a sulfonate that can be used in the current compositions is sodium C14-16 olefin sulfonate.

In an embodiment, the anionic surfactant ((c)(ii)(2)) is selected from sodium cocoyl glycinate, sodium laureth sulfate, sodium cocoyl taurate, and mixtures thereof.

The at least one anionic surfactant (c)(ii)(2) is present in a total amount ranging from about 2% to about 8% by weight, typically from about 2.5% to about 5%, more typically about 3% by weight, including all ranges and sub ranges therebetween, based on the total weight of the composition as a whole.

Water (Component (d))

The compositions of the invention are aqueous and comprise from about 40% to about 88% water, particularly from about 60% to about 85%, more particularly from about 75% to about 83%, most typically from about 80% to about 82% water.

Optional Additives

The composition of the present disclosure may additionally include any other adjuvant or additive that is usually used in the field of self-cleaning products, in particular shampoos. A person skilled in the art would know which adjuvants and/or additives to select to achieve the desired results (e.g. preservatives) without adversely affecting the properties of claimed emulsions. For example, such additives include pH adjusting agents, preserving agents, sequestrants and chelators, consistency regulators (e.g. isopropyl alcohol), thickeners, antioxidants, fragrances, dyestuffs such as soluble dyes and pigments, optical brighteners, electrolytes and stabilizers (e.g. sodium chloride, glycerin), plant extracts, proteins, amino acids, vitamins, glycols, emollients, derivatives of the foregoing, and mixtures thereof. Such additives are described, for example in US2012/0308492 at [0079]-[0080] and US2006/0217283 at [0084]-[0087], both of which are herein incorporated by reference. These additives may be hydrophobic or hydrophilic.

Non-limiting examples of pH adjusting agents include potassium acetate, potassium hydroxide, sodium carbonate, sodium hydroxide, phosphoric acid, succinic acid, sodium citrate, citric acid, boric acid, lactic acid, sodium hydrogen carbonate, ethanol amines, and mixtures thereof. In a particular embodiment, the pH adjusting agent is selected from potassium hydroxide, sodium hydroxide, ethanol amines, and mixtures thereof. In a particular embodiment, the pH adjusting agent is selected from sodium hydroxide, potassium hydroxide and ethanol amines, and mixtures thereof.

Non-limiting examples of useful preservatives include ethanol, polyvinyl alcohol, phenoxyethanol, benzyl alcohol, salicylic acid, sodium benzoate, caprylyl glycol, methyl paraben, propyl paraben, ethylhexylglycerin, 1,3-propanediol, cholrphensin, methylchloroisothiazolinone, methylisothiazolinone, benzalkonium chloride, polyaminopropyl biguanide, and mixtures thereof. In a particular embodiment, the pH adjusting agent is selected from cholrphensin, methylchloroisothiazolinone, methylisothiazolinone, benzalkonium chloride, polyaminopropyl biguanide, and mixtures thereof.

Chelating agents and antioxidants are ingredients which assist in preventing or retarding spoilage. Examples of antioxidants suitable for use in the present composition are potassium sulfite, sodium bisulfite, sodium erythrobate, sodium metabisulfite, sodium sulfite, propyl gallate, cysteine hydrochloride, butylated hydroxytoluene, butylated hydroxyanisole, and mixtures thereof. Suitable chelators include salts of ethylenediaminetetraacetic acid ("EDTA"), butylated hydroxytoluene ("BHT"), and mixtures thereof.

Other than some possible byproduct electrolytes that may be present in some commercial formulations of raw materials, no additional electrolytes are present/added to the inventive compositions.

The cleansing compositions of the present invention have a pH of about 9 or less, more typically between about 8 and about 4.5. Additionally, the cleansing compositions are preferably clear.

Rheology

The compositions of the invention have a tan delta greater than 1 at rest and less than 1 at relatively low oscillating frequency. The crossover frequency at which the compositions of the invention change behavior from a liquid (G">G') to a solid (G'>G") is from about 0.1 to about 30 rad/s, typically from about 2 rad/s to about 25 rad/s, more typically from about 3.2 rad/s to about 22 rad/s. As seen from the above cross-over frequencies, the present compositions possess a "jiggling" behavior at a wide range of frequencies.

The compositions have an elastic modulus (G') of from about 0.023 to about 2 and a viscous modulus (G") of from about 0.05 to about 26 at low oscillating frequencies of 0.1 rad/sec.

In an embodiment, the present invention relates to an aqueous cleaning and conditioning composition comprising:
- (a) from about 6% to about 20% of at least one nonionic surfactant;
- (b) from about 3% to about 10% of at least one amphoteric surfactant;
- (c) at least one material selected from
  - (i) from about 0.1% to about 10% of at least one nonionic thickener;
  - (ii) (1) from about 0.01% to about 5% of at least one cationic agent combined with
    - (2) from about 2% to about 8% of an anionic surfactant; and
  - (iii) from about 0.01 to about 23% of a mixture of from about 0.1% to about 10% of nonionic thickener (c)(i) combined with from about 0.01% to about 5% of a cationic agent (c)(ii)(1), and/or from about 2% to about 8% of an anionic surfactant (c)(ii)(2); and
- (d) from about 40% to about 88% water;

wherein the ratio of the amount of (the sum of nonionic surfactant (a)+amphoteric surfactant (b)) to the amount of anionic surfactant ((c)(ii)(2)) is greater than 2:1.

In a particular embodiment, the present invention relates to an aqueous cleaning and conditioning composition comprising:
- (a) from about 6% to about 20% of at least one nonionic surfactant;
- (b) from about 3% to about 10% of at least one amphoteric surfactant;
- (c) at least one material selected from
  - (i) from about 0.1% to about 10% of at least one nonionic thickener;
  - (ii) (1) from about 0.01% to about 5% of at least one cationic agent combined with
    - (2) from about 2% to about 8% of an anionic surfactant; and
  - (iii) from about 0.01 to about 23% of a mixture of from about 0.1% to about 10% of nonionic thickener (c)(i) combined with from about 0.01% to about 5% of a cationic agent (c)(ii)(1), and/or from about 2% to about 8% of an anionic surfactant (c)(ii)(2); and
- (d) from about 40% to about 88% water;

wherein the amount of the nonionic surfactant (a) present in the final composition is greater than the amphoteric surfactant (b); the ratio of the amount of nonionic surfactant (a) to the amount of anionic surfactant (c)(ii)(2) is from about 2:1 to about 5:1; and the composition has a cross over frequency of from about 0.1 rad/s to about 30 rad/s; the percent amounts being based on the weight percent of each component in the final composition.

In a particular embodiment, the present invention relates to an aqueous cleaning and conditioning composition comprising:
- (a) from about 6% to about 20% of at least one nonionic surfactant;
- (b) from about 3% to about 10% of at least one amphoteric surfactant;
- (c) at least one material selected from
  - (i) from about 0.1% to about 10% of at least one nonionic thickener;
  - (ii) (1) from about 0.01% to about 5% of at least one cationic agent combined with
    - (2) from about 2% to about 8% of an anionic surfactant; and
  - (iii) from about 0.01% to about 23% of a mixture of from about 0.1% to about 10% of nonionic thickener (c)(i) combined with from about 0.01% to about 5% of a cationic agent (c)(ii)(1), and/or from about 2% to about 8% of an anionic surfactant (c)(ii)(2); and
- (d) from about 40% to about 88% water;

wherein the amount of the nonionic surfactant (a) present in the final composition is greater than the amphoteric surfactant (b); the ratio of the amount of nonionic surfactant (a) to the amount of anionic surfactant (c)(ii)(2) is from about 2:1 to about 5:1; the ratio of the amount of (nonionic surfactant+amphoteric surfactant)

to the amount of anionic surfactant is greater than 2:1; and the composition has a cross over frequency of from about 0.1 rad/s to about 30 rad/s; the percent amounts being based on the weight percent of each component in the final composition.

The present invention is also directed to a process for cleansing and conditioning a keratinous substrate involving contacting the keratinous substrate with the above-disclosed cleansing composition. Preferably the keratinous substrate is hair.

Designations of each component in the Examples Tables:
A=nonionic surfactant. Lauryl glucoside was used in examples unless otherwise stated
B=amphoteric surfactant. Cocoamidopropyl betaine was used in examples unless otherwise stated
C=nonionic thickener. PEG-55 propylene glycol oleate unless otherwise stated
D=cationic agent. PQ-6 was used unless otherwise stated
E=anionic surfactant. Cocoyl glycinate was used unless otherwise stated

TABLE 1

Examples 1-5: Compositions Having Various Surfactant Substitutions

|  | INCI US | Ex 1 | Ex 2 | Ex 3 | Ex 4 | Ex 5 |
| --- | --- | --- | --- | --- | --- | --- |
| Nonionic surfactant (A) | LAURYL GLUCOSIDE (a) | 7.15 | 7.15 | 7.15 | 7.15 | 7.15 |
| Amphoteric surfactant (B) | COCAMIDOPROPYL BETAINE (b) | 5.7 | | | | |
| Amphoteric surfactant (B) | COCOBETAINE(b) | | 5.7 | | | |
| Amphoteric surfactant (B) | SODIUM COCOAMPHOPROPIONATE (b) | | | 5.7 | 5.7 | 5.7 |
| Nonionic Thickener (C) | PEG-55 PROPYLENE GLYCOL OLEATE (c)(i) | 0.4 | 0.4 | 0.4 | 0.4 | 0.4 |
| Nonionic Thickener (C) | PEG-8 (c)(i) | | | | | |
| Anionic Surfactant (E) | SODIUM COCOYL GLYCINATE (c)ii(2) | 3 | 3 | 3 | | |
| Anionic Surfactant (E) | SLES (c)(ii)(2) | | | | 3 | |
| Anionic Surfactant (E) | SODIUM COCOYL TAURATE (c)(ii)(2) | | | | | 3 |
| Cationic agent (D) | POLYQUATERNIUM-22 (c)(ii)(1) | 0.94 | 0.94 | 0.94 | 0.94 | 0.94 |
| Cationic agent (D) | PQ-6 (c)(ii)(1) | | | | | |
| Cationic agent (D) | CTAC (c)(ii)(1) | | | | | |
|  | WATER (d) | 81.84 | 81.84 | 81.84 | 81.84 | 81.84 |
| Appearance | Crushed Ice Gel | X | X | X | | X |
| Appearance | Crushed ice/Rigid Gel | | | | X | |
| Cross Over Frequency |  | 6.3 | | | 3.2 | |

Notwithstanding that the numerical ranges and parameters setting forth the broad scope of the invention are approximations, the numerical values set forth in the specific examples are reported as precisely as possible. Any numerical value, however, inherently contain certain errors necessarily resulting from the standard deviation found in their respective measurements. The following examples are intended to illustrate the invention without limiting the scope as a result. The percentages are given on a weight basis unless otherwise specified.

EXAMPLES

Preparation:

The compositions of the examples below were prepared by combining all of the surfactants/agents, heating to 50° C. and mixing until the mixture was uniform. The mixture was then allowed to cool to room temperature.

The compositions varied in appearance. The compositions of Examples 1-9 were clear gel-like compositions. Depending on the surfactants used, the compositions were colorless, yellow or brownish. Clarity of the compositions was measured by the transmittance percentage of light with a wavelength of 700 nm by UV-visible spectrophotometry.

TABLE 2

Examples 6-9: Compositions Having Various Surfactant Substitutions

|  | INCI US | Ex 6 | Ex 7 | Ex 8 | Ex 9 |
| --- | --- | --- | --- | --- | --- |
| Nonionic surfactant (A) | LAURYL GLUCOSIDE (a) | 7.15 | 7.15 | 7.15 | 7.15 |
| Amphoteric surfactant (B) | COCAMIDO-PROPYL BETAINE (b) | | | | |
| Amphoteric surfactant (B) | COCOBETAINE (b) | | | | |
| Amphoteric surfactant (B) | SODIUM COCOAMPHO-PROPIONATE (b) | 5.7 | 5.7 | 5.7 | 5.7 |
| Nonionic Thickener (C) | PEG-55 PROPYLENE GLYCOL OLEATE (c) (i) | 0.4 | | | |
| Nonionic Thickener (C) | PEG-8 (c) (i) | | 1 | | |
| Anionic Surfactant (E) | SODIUM COCOYL GLYCINATE (c) (ii) (2) | | 3 | 3 | 3 |
| Anionic Surfactant (E) | SLES (c) (ii) (2) | | | | |

TABLE 2-continued

Examples 6-9: Compositions Having Various Surfactant Substitutions

|  | INCI US | Ex 6 | Ex 7 | Ex 8 | Ex 9 |
|---|---|---|---|---|---|
| Anionic Surfactant (E) | SODIUM COCOYL TAURATE (c) (ii) (2) | | | | |
| Cationic agent (D) | POLY-QUATERNIUM-22 (c) (ii) (1) | 0.94 | 0.94 | | |
| Cationic agent (D) | PQ-6 (c) (ii) (1) | | | 1 | |
| Cationic agent (D) | CTAC (c) (ii) (1) | | | | 1 |
|  | WATER (d) | 81.84 | 81.84 | 81.84 | 81.84 |
| Appearance | Ringing Gel/Jiggling Gel | X | | | |
| Appearance | Vibrating/Stretching Gel | | X | | |
| Appearance | Ringing Gel | | | X | X |
| Cross Over Frequency | | 22 hz | | | |

Table 3 below exemplifies the requirement for certain key components as well as the combination of components that enable the creation of the structured phase compositions of the invention.

TABLE 3

Compositions Demonstrating Impact of Components C, D and E

| Composition | Component | Variables | Description | Rheology Result* |
|---|---|---|---|---|
| Comp 2 | A + B + E + C | 1% C | Standard positive control | Positive |
| Comp 22 (Example 1) | A + B + E + C | 2% C | Standard positive control | Positive |
| Comp 16 | [B + E + C] | No A | Negative control | Negative |
| Comp 6 (Example 2) | A + B + E + C | B = coco-betaine | Positive control | Positive |
| Comp 8 | A + B + E + C | B = cocoamphodi-propionate | Positive control | Positive |
| Comp 7 (Example 3) | A + B + E + C | B = Disodium cocoampho-diacetate | Positive control | Positive |
| 15 | [A + E + C] | No B | Negative control | Phase separation |
| Comp 11 (Example 4) | A + B + E + C | E = SLES | Positive control | Positive |
| Comp 12 (Example 5) | A + B + E + C | E = Taurate | Positive control | Positive |
| Comp 9 | A + B + E + C | E = Isethionate | Positive control | Positive |
| Comp 17 Example 6 | A + B + C | No E | Positive control | Positive |
| Comp 18 (Example 7) | A + B + E + C | C = PEG-8 | Positive control | Positive |
| Comp 13 | A + B + E + C | C = PEG-180 | Positive control | Positive |
| Comp 1 | [A + B + E] | No C, no D | Negative control | Negative |
| Comp 23 | [A + B + D] | D = PQ-6 (LMW), no E | Negative control | Negative |
| Comp 24 Example 8 | A + B + E + D | D = PQ-6 (LMW) | Positive control | Positive |
| Comp 25 | A + B + E + D | D = Amine | Positive control | Positive |

TABLE 3-continued

Compositions Demonstrating Impact of Components C, D and E

| Composition | Component | Variables | Description | Rheology Result* |
|---|---|---|---|---|
| Comp 26 (Example 9) | A + B + E + D | D = CETAC | Positive control | Positive |
| Comp 27 | A + B + E + C | E = SCI | Positive control | Positive |
| Comp 28 | [A + B] |  | control | Negative |

*In Table 3 above a "positive" result indicates a clear gel phase that macroscopically exhibits solid behavior when sheared or touched and has a cross over frequency between 0.1 and 30 rads. A negative result indicates that the resulting composition was a liquid non-gel formula, and/or the composition did not have a cross over frequency between 0.1 and 30 rads, and/or the composition was not stable and separted into different phases.

As evidenced from the results reported in Table 3:

Composition 16 shows that a nonionic surfactant (A) is required to create the structured composition of the invention;

Composition 15 shows that the amphoteric surfactant (B) is also required;

Composition 17 shows that a combination of nonionic surfactant (A)+amphoteric surfactant (B)+nonionic thickener (C) will work while Composition 28 shows that A+B alone will not work;

Composition 1 shows that a combination of nonionic surfactant (A)+amphoteric surfactant (B)+anionic surfactant (E) alone will not yield the claimed compositions while Composition 24 shows that the addition of cationic agent (D) to (A)+(B)+(E) will yield a composition having the desired rheological properties; and Composition 23 shows that a combination of nonionic surfactant (A)+amphoteric surfactant (B)+cationic agent (D) alone will not yield the inventive compositions but upon adding anionic surfactant (E) then the desired composition is achieved as demonstrated in Composition 25.

Rheological Evaluation

Protocols

The rheological properties of sample formulas were tested as follows.

Instrument: ARES-G2 Rheometer

Geometry: 20 mm 2° steel cone

Sample formulas were loaded in the rehometer and allowed to reach 25° C. Equilibration of 60 seconds relaxation was allowed prior to testing. A frequency sweep was conducted between 0.1-200 rad/s. Strain percentage was controlled at 10%.

The following parameters were measured and the results reported below in Table 4:

G'=Elastic modulus (solid behavior).

G"=Viscous modulus (liquid behavior).

Values of G' and G" were reported at low frequency (0.1 rad/s) and high frequency (200 rad/s).

Cross over frequency: The frequency at which the G' and G" curves intersect. This is the point at which the formula behavior changed from predominantly liquid behavior (G">G") to predominantly solid behavior (G'>G").

TABLE 4

Rheological Measurements

| Example | Component | Variables | G' (0.1 rad/s) | G" (0.1 rad/s) | G' (200 rad/s) | G" (200 rad/s) | Cross over freq (rad/s) (Cross to Solids) |
|---|---|---|---|---|---|---|---|
| Ex 6 (Comp 17) | A + B + C | No E | 0.2309 | 1.855 | 308.8 | 139.6 | 22 |
| Ex 1 (Comp 22) | A + B + C + E | | 0.1966 | 8.067 | 664 | 175.5 | 6.31 |
| Ex 4 (Comp 11) | A + B + C + E | E-SLES | 0.5538 | 13.73 | 604.3 | 145.9 | 3.16 |
| Comp 27 | A + B + C + E | E-SCI | 1.641 | 25.74 | 951.2 | 212.9 | 2 |
| Ex 8 (Comp 24) | A + B + E + D | | 0.02301 | 0.9617 | 52.89 | 60.54 | 9 |

As is shown in Tables 3 and 4 above, a combination of nonionic surfactant (A)+amphoteric surfactant (B)+a nonionic thickener (C) yields a composition with the desired rheological profile. The addition of an anionic surfactant (E) to the foregoing compositions broadens the range of the plastic (solid) phase of the composition. If the nonionic thickener (C) is eliminated, both the cationic agent (D) and anionic surfactant (E) are necessary to yield the desired rheology.

What is claimed is:

1. An aqueous cleansing composition comprising:
   (a) from about 6% to about 20% of at least one nonionic surfactant;
   (b) from about 3% to about 10% of at least one amphoteric surfactant selected from the group consisting of betaines, sultaines, amphoacetates, amphoprionates, and mixtures thereof;
   (c)
   (1) from about 0.01% to about 5% of at least one cationic agent selected from the group consisting of cationic polymers, cationic amines, cationic silanes, and mixtures thereof; combined with
   (2) from about 2% to about 8% of an anionic surfactant selected from the group consisting of alkyl sulfates, alkyl ether sulfates, acyl isethionates, acyl glycianates, acyl taurates, acyl amino acids, acyl sarcosinates, sulfosuccinates, sulfonates, alkyl polyglucoside sulfonates and alkyl polyglucoside carboxylates, wherein the alkyl and acyl groups of all these compounds comprise from 6 to 24 carbon atoms; and
   (d) from about 40% to about 88% water;
   wherein the amount of the nonionic surfactant (a) present in the final composition is greater than the amount of amphoteric surfactant (b),
   wherein the composition has a cross over frequency of from about 0.1 rad/s to about 30 rad/s,
   wherein the percent amounts being based on the weight percent of each component in the final composition, and
   wherein the pH of the composition is from 4.5 to 8.

2. The composition of claim 1 wherein the ratio of (the sum of the amount of nonionic surfactant (a)+amount of amphoteric surfactant (b)) to the amount of anionic surfactant (c)(2) is greater than 2:1.

3. The composition of claim 2 wherein the ratio is at least 4:1, based on the weight percent of each component in the final composition.

4. The composition of claim 1 wherein the sum of the amount of cationic agent (c)(1) plus anionic surfactant (c)(2) is from about 0.01 to about 13, based on the weight percent of each component in the final composition.

5. The composition of claim 1 wherein the nonionic surfactant (a) is an alkyl polyglucoside.

6. The composition of claim 5 wherein the alkyl polyglucoside is selected from the group consisting of lauryl glucoside, octyl glucoside, decyl glucoside, coco glucoside, and mixtures thereof.

7. The composition of claim 1, wherein the amphoteric surfactant (b) is a betaine selected from the group consisting of a coco betaine, cocoamidopropyl betaine, lauryl betaine, laurylhydroxy sulfobetaine, lauryldimethyl betaine, cocoamidopropyl hydroxysultaine, behenyl betaine, capryl/capramidopropyl betaine, lauryl hydroxysultaine, stearyl betaine, and mixtures thereof.

8. The composition of claim 1, wherein the amphoteric surfactant (b) is sodium cocamphoprionate.

9. The composition of claim 1, wherein the cationic agent (c)(1) is selected from the group consisting of polyquaternium-10 ("PQ-10"), guar hydroxypropyltrimonium chloride; diallyldimethyl ammonium chloride, polyquaternium-4 (PQ-4), polyquaternium-5 (PQ-5), polyquaternium-6 (PQ-6), polyquaternium-7 (PQ-7), polyquaternium-22 (PQ-22), polyquaternium-37 (PQ-37), polyquaternium-39 (PQ-39), polyquaternium47 (PQ-47), polyquaternium-53 (PQ-53), hydroxypropyltrimonium, hydrolyzed wheat protein and mixtures thereof.

10. The composition of claim 1, wherein the cationic agent (c)(1) is selected from the group consisting of 3-mercaptopropyltriethoxysilane, 3-aminopropyltriethoxysilane, and mixtures thereof.

11. The composition of claim 1, wherein the cationic agent (c)(1) is selected from the group consisting of PQ-6 and PQ-22 cetyltrimethylammonium chloride.

12. The composition of claim 1, wherein the anionic surfactant (c)(2) is selected from the group consisting of sodium laureth sulfate, sodium cocoyl isethionate, sodium lauroyl methyl isethionate, sodium cocoyl glycinate, sodium cocoyl taurate, sodium methyl cocoyl taurate, sodium cocoyl glycinate, potassium cocoyl glycinate, sodium lauryl sarcosinate, sodium cocoyl alaninate, sodium cocoyl alanine, the salts thereof, and mixtures thereof.

13. The composition of claim 12 wherein the anionic surfactant (c)(2) is selected from the group consisting of sodium cocoyl glycinate, sodium laureth sulfate, sodium cocoyl taurate, and mixtures thereof.

14. A method of cleansing and conditioning hair comprising contacting the hair with an aqueous cleansing composition according to claim 1.

15. An aqueous cleansing composition comprising:
   (a) from about 6% to about 20% of at least one alkyl polyglucoside;
   (b) from about 3% to about 10% of at least one amphoteric surfactant selected from the group consisting of a betaine, a sultaine, an amphoacetate, an amphoprionate, and mixtures thereof;

(c)
- (1) from about 0.01% to about 5% of at least one cationic agent selected from the group consisting of cationic polymers, cationic amines, cationic silanes, and mixtures thereof combined with
- (2) from about 2% to about 8% of an anionic surfactant selected from the group consisting of sodium laureth sulfate, sodium cocoyl isethionate, sodium lauroyl methyl isethionate, sodium cocoyl glycinate, sodium cocoyl taurate, sodium methyl cocoyl taurate, sodium cocoyl glycinate, potassium cocoyl glycinate, sodium lauryl sarcosinate, sodium cocoyl alaninate, sodium cocoyl alanine, the salts thereof, and mixtures thereof; and (d) from about 40% to about 88% water;

wherein the amount of the nonionic surfactant (a) present in the final composition is greater than the amount of amphoteric surfactant (b), wherein the composition has a cross over frequency of from about 0.1 rad/s to about 30 rad/s, wherein the percent amounts being based on the weight percent of each component in the final composition, and wherein the pH of the composition is from 4.5 to 8.

16. The aqueous cleansing composition according to claim 15, wherein the composition is clear.

17. An aqueous cleansing composition according to claim 1 wherein the composition further contains from about 0.1% to about 10% of at least one nonionic thickener.

* * * * *